(12) United States Patent
Lillegaard

(10) Patent No.: US 7,476,220 B2
(45) Date of Patent: Jan. 13, 2009

(54) COLLECTING BAG HAVING AN ACCOMMODATING MEANS FOR A CLOSURE DEVICE

(75) Inventor: Jens Lillegaard, Humlebæk (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 10/511,168

(22) PCT Filed: Apr. 14, 2003

(86) PCT No.: PCT/DK03/00253

§ 371 (c)(1),
(2), (4) Date: Jul. 25, 2005

(87) PCT Pub. No.: WO03/086249

PCT Pub. Date: Oct. 23, 2003

(65) Prior Publication Data

US 2005/0273065 A1    Dec. 8, 2005

(30) Foreign Application Priority Data

Apr. 17, 2002  (DK) .............................. 2002 00568

(51) Int. Cl.
A61M 1/00 (2006.01)
A47K 11/00 (2006.01)
A61F 5/44 (2006.01)

(52) U.S. Cl. ..................... 604/342; 604/317; 604/332; 604/338; 4/144.2

(58) Field of Classification Search ......... 604/317–345; 4/144.1–144.3
See application file for complete search history.

(56) References Cited

U.S. PATENT DOCUMENTS

| 3,721,243 | A | | 3/1973 | Hesterman et al. |
| 3,865,165 | A | | 2/1975 | Glass |
| 3,926,233 | A | | 12/1975 | Brendling |
| 4,084,590 | A | | 4/1978 | Caraway et al. |
| 4,213,458 | A | * | 7/1980 | Nolan et al. ................. 604/344 |
| 4,306,029 | A | | 12/1981 | Carpenter |
| 4,449,971 | A | * | 5/1984 | Cawood ...................... 604/544 |
| 4,519,797 | A | | 5/1985 | Hall |
| 4,790,834 | A | * | 12/1988 | Austin ......................... 604/349 |
| 5,403,299 | A | * | 4/1995 | Schneider .................... 604/332 |
| 6,206,864 | B1 | * | 3/2001 | Kavanagh et al. ........... 604/332 |
| 6,849,066 | B1 | | 2/2005 | Ciok et al. |

FOREIGN PATENT DOCUMENTS

| DE | 1 997 801 U | 12/1968 |
| DE | 24 35 945 | 2/1975 |
| DE | 34 43 918 A1 | 6/1986 |

(Continued)

*Primary Examiner*—Tatyana Zalukaeva
*Assistant Examiner*—Melanie J Hand
(74) *Attorney, Agent, or Firm*—Jacobson Holman PLLC

(57) ABSTRACT

The collecting bag comprises a bag member (1) and a discharge portion (6) including a closure device (7). An accommodating means (8) is provided within the outer contours of the bag member for accommodating at least a part of the discharge portion in the position of use of the bag. The accommodating means includes a slit (20) in the comfort layer (52) overlying the front film blank (2), such that a part of the discharge portion may be lodged in the space between joint sections that connect inner tubular film elements with the film blanks of the bag member.

21 Claims, 6 Drawing Sheets

FOREIGN PATENT DOCUMENTS

| | | |
|---|---|---|
| EP | 0 711 536 A1 | 5/1996 |
| WO | WO 91/00074 | 1/1991 |
| WO | WO 93/17643 | 9/1993 |
| WO | WO 01/21115 A1 | 3/2001 |
| WO | WO 0121115 A1 * | 3/2001 |

* cited by examiner

COLLECTING BAG HAVING AN ACCOMMODATING MEANS FOR A CLOSURE DEVICE

This is a nationalization of PCT/DK03/00253 filed Apr. 14, 2003 and published in English.

FIELD OF THE INVENTION

The present invention relates to a collecting bag for human body wastes, comprising a bag member including at least two outer film blanks with joined edges defining the outer contours of the bag member, an inlet opening provided in one of said film blanks, a discharge portion at a distance from the inlet opening, in a lower portion of the bag member, including a closure device for bringing the bag from a discharge position, in which the bag is open, to a position of use, in which the bag is closed, the discharge portion defining a longitudinal direction, and accommodating means within the outer contours of the bag member for accommodating at least a part of the discharge portion in the position of use of the bag.

BACKGROUND OF THE INVENTION

In such collecting bags it is usually a desire to attach at least a part of the discharge portion temporarily to the bag member in the position of use of the bag in order to attain a compact appearance in this position and to prevent the discharge portion and the closure device from dangling which might be uncomfortable to the user.

In bags having an elongated, substantially flat discharge portion, this portion may be folded or rolled up in the direction of the bag member, and subsequently temporarily secured to the bag member, partly in order to close the bag and partly to attain said compact appearance and the attachment to the bag member.

However, in collecting bags having a closure device of some extent, eg. a valve or a clamp, these solutions may not be applied.

U.S. Pat. No. 4,519,797 discloses a cover for an ostomy pouch having a drain fitting at the bottom of the pouch. The cover has an opening allowing the pouch to be mounted in the usual manner on the plate worn by the patient. The cover has an integral pocket which receives the drain fitting to prevent irritation to the sensitive portions of the anatomy.

This solution, however, while preventing the drain fitting from directly contacting sensitive portions of the anatomy, contributes to the bulkiness of the pouch, thereby compromising the demand for discretion.

U.S. Pat. No. 4,449,971 discloses a collecting bag of the initially stated kind, in which the accommodating means in the form of a pocket having an entrance slit is formed on an extension of the bag member. Similar arrangements are shown in e.g. U.S. Pat. Nos. 3,865,165 and 4,306,029.

In all of the above arrangements the outer contours of the bag are widened due to the accommodating means, thus making the overall size of the bag larger.

Applicant's international published application No. WO 01/21115 discloses a collecting bag of the initially stated kind, in which the accommodating means is provided by means of an open receptacle formed within the outer contours of the bag member and having a basis portion in which the outer film blanks are undetachably connected with each other, the periphery of the basis portion being situated at a distance from the joined edges of the bag member and the discharge portion.

This arrangement provides for a collecting bag, in which the closure device may be lodged in its entirety in the accommodating means without protruding outside the arched planes formed by the film blanks when the bag is expanded by its contents, and the outer contours of which are not affected by the accommodating means.

However, a reduction of the volume available for body wastes in the remaining portion of the bag is unavoidable due to the size of the basis portion, even if the dimensions of the basis portion are adapted to those of the closure device. Furthermore, this collecting bag has some tendency of blocking the passageway to the outlet if, eg., the user exerts a pull in the discharge portion during emptying of the bag, and has moreover some tendency of twisting in the position of use.

SUMMARY OF THE INVENTION

With this background it is an object of the present invention to improve a collecting bag of the kind mentioned in the introduction such that the dimensions and the volume available for body wastes are optimised while retaining the comfort and discretion for the user.

This and further objects are met by the provision of a collecting bag of the kind mentioned in the introduction which is characterized in that said bag member includes at least a first and a second substantially tubular inner film element, each substantially tubular inner film element being attached to the inner side of each outer film blank by means of at least one joint, said first and second substantially tubular inner film element being situated at a respective side of a dividing line substantially parallel with the longitudinal direction defined by the discharge portion and having, when the bag is substantially empty, a distal and a proximal fold with respect to said dividing line, that the joint between the first substantially tubular inner film element and one outer film blank and between the second substantially tubular inner film element and said one outer film blank includes at least one proximal joint section at or near the proximal fold and at least one distal joint section at or near the distal fold, the distance between at least a lower part of the proximal joint section and the proximal fold being smaller than the distance between at least a lower part of the distal joint section and the distal fold, and that said accommodating means includes an element providing at least one opening for receiving at least a part of the discharge portion in the position of use of the bag, said opening extending substantially transversely between the proximal joint sections of the first and the second substantially tubular inner film element, respectively.

By providing the bag member with such substantially tubular inner film elements, the requirements to a collecting bag having a large available volume and a non-bulging bag member are fulfilled, and at the same time, the provision of joints between the substantially tubular inner film elements and the film blank having a proximal section, of which at least the lower part is situated at a smaller distance from the proximal fold than the corresponding part of the distal joint section with respect to the distal fold, ensures that sufficient space for the discharge portion is created in the bag member.

In a preferred embodiment, at least the proximal section of the joint between the first and second substantially tubular inner film element, respectively, and said one outer film blank extends obliquely with respect to said dividing line such that said joint sections converge in the direction of the discharge portion. This provides for an optimum balance between the requirements as to the available volume and the comfort to the user, as the accommodating means created between the two substantially tubular inner film elements is substantially wedge-shaped.

In an advantageous further development of this embodiment, the distance between the distal joint section and the distal fold is larger than the distance between the lower part of the proximal joint section and the proximal fold and smaller than the distance between the upper part of the proximal joint section and the proximal fold.

The angle of inclination between each oblique joint section and the dividing line preferably lies in the range from 5° to 60°. The choice of a suitable angle of inclination is made in consideration of the desired volume of the bag and the dimensions of the discharge portion and the tubular film elements.

The distance between the lower ends of the oblique joint sections preferably corresponds substantially to the cross-sectional dimensions of the corresponding part of the discharge portion. In this manner, the volume reduction caused by the accommodating means is as small as possible.

In an alternative embodiment, the proximal joint section is substantially parallel with the proximal fold, such that the distance between the proximal joint section and the proximal fold is substantially uniform, and said distance is smaller than the distance between the distal joint section and the distal fold.

In order to reduce the volume available for the contents of the bag as little as possible, the distance between the proximal joint sections preferably corresponds substantially to the cross-sectional dimensions of the corresponding part of the discharge portion.

In an advantageous embodiment, the discharge portion receiving opening is designed as a slit in a comfort layer overlying the film blank in question. The provision of a comfort layer makes the collecting bag simple to manufacture and furthermore entails that it is possible to make the contents of the collecting bag invisible from the outside, even if the film blanks are made from a transparent material, and furthermore, the comfort layer makes the collecting bag more comfortable to handle and wear.

In order to protect the comfort layer from tearing or rupturing, a reinforcing layer may be inserted between the comfort layer and the film blank, at least in the area of the slit.

The joint sections may at the ends of the sections be reinforced by means of spots containing reinforcing material, spot welding, a continuing portion etc.

In addition to the two substantially tubular inner film elements bordering the accommodating means, further substantially tubular inner film elements may be provided in the bag member in order to control the thickness of the bag member in its filled condition.

Preferably, each substantially tubular inner film element is provided in the area of the bag member situated near the discharge portion.

The bag member may be substantially symmetrical with respect to said dividing line.

Further features and advantages may readily be appreciated from the following detailed description.

BRIEF DESCRIPTION OF THE DRAWINGS

In the following the invention will be described in further detail with reference to the schematic drawings, in which.

DETAILED DESCRIPTION OF PREFERRED EMBODIMENTS

Figure 1:
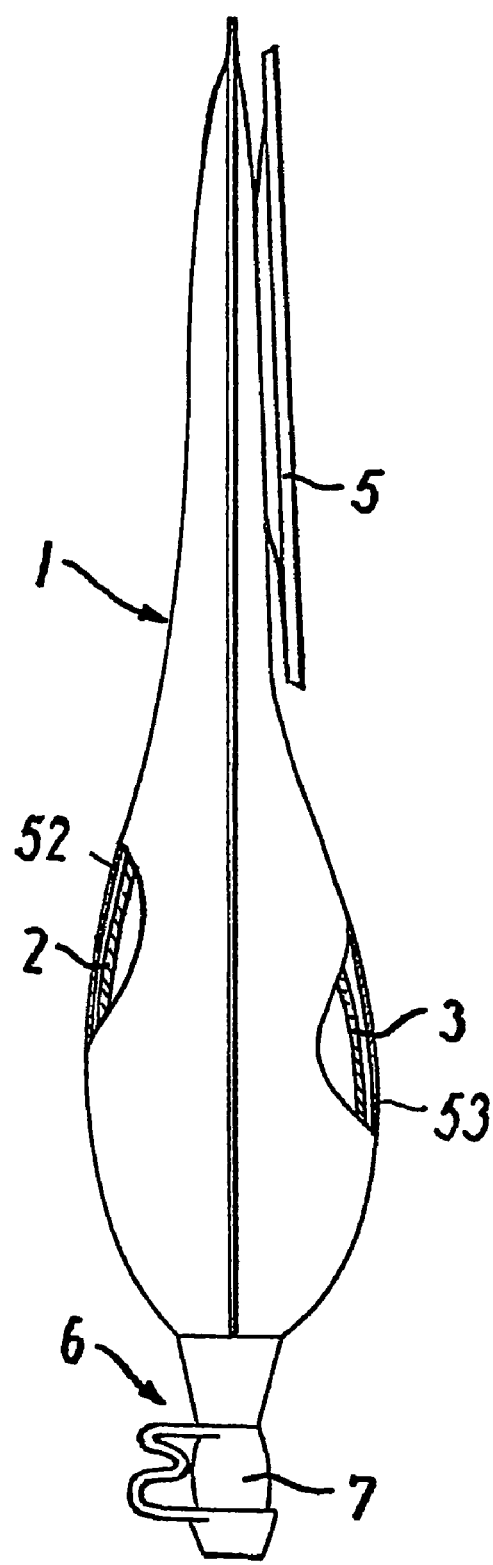
FIG. 1 shows a side view, partly sectional, of a collecting bag according to the invention in a discharge position, the bag being shown in the shape it assumes when at least partly filled.
Figure 2:
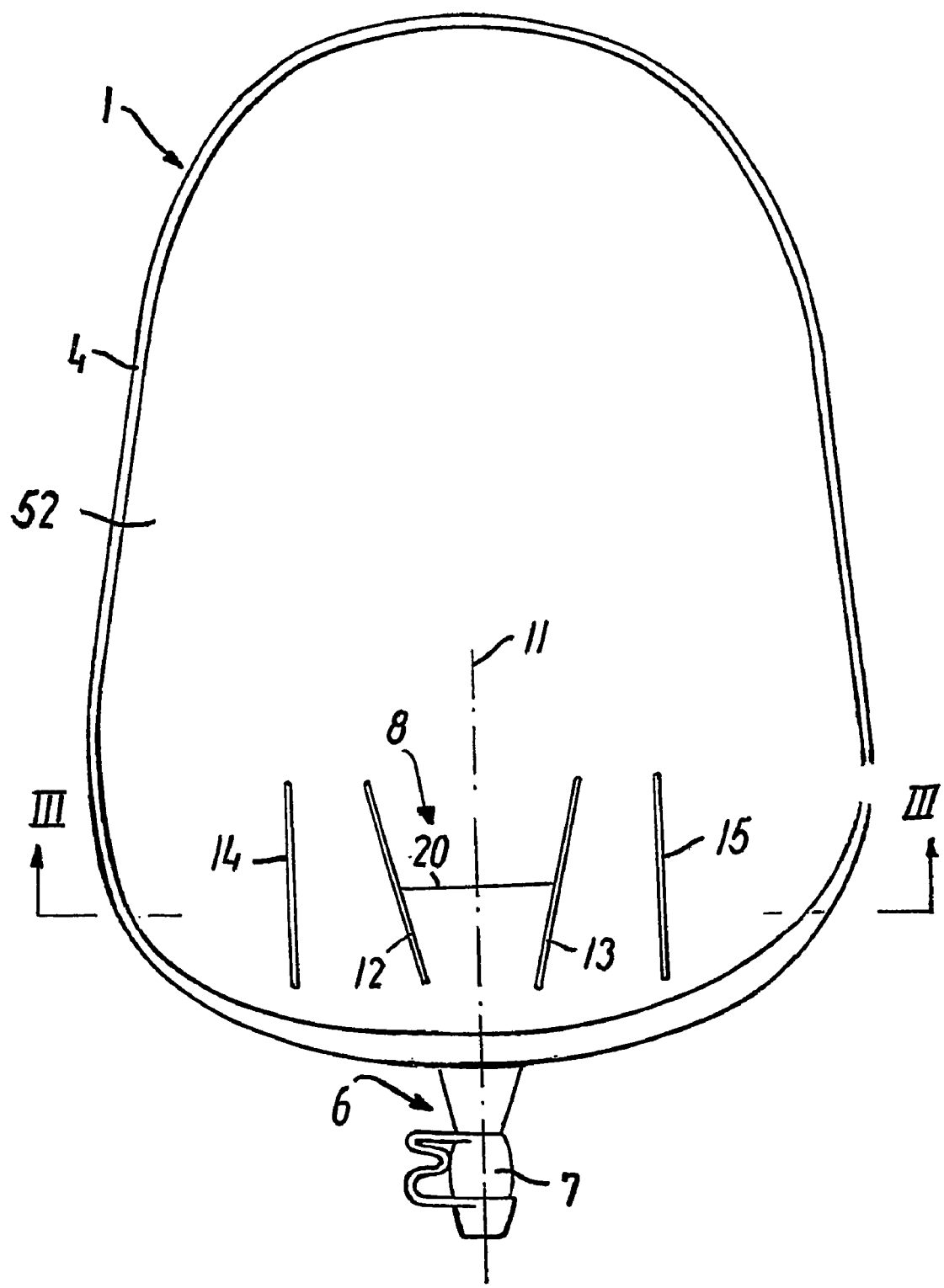
FIG. 2 shows a plan view of the collecting bag shown in FIG. 1.

The collecting bag shown in the drawings comprises a bag member 1 formed by two film blanks 2,3 which are joined along their edges by means of a seam 4 made by welding or in any other convenient manner and defining the outer contours of the bag member. The film blanks may be made from any suitable flexible plastic sheet or foil material. In order to make the bag more comfortable to wear and/or to make the contents of the bag invisible in the case of transparent film blanks, a comfort layer 52,53 is provided overlying a respective film blank 2,3. The comfort layers may be made from a nonwoven material or any other suitable material having the desired properties.

In the film blank 3 which in use is intended to face the user and thus forms the back wall of the bag, an inlet opening, not shown, is provided. The inlet opening is, in a manner known per se, surrounded by connecting elements 5 for connection of the bag to a body orifice in the form of a so-called stoma in the user's abdominal wall, or for connection with a tube member in the case of a urine-incontinence bag, Optionally, a reflux valve is in a manner known per se arranged between the inlet opening and the lower portion of the bag member. In this respect it is noted that terms such as 'upper' and 'lower' etc. only refer to the position shown in the drawings, corresponding to the position the bag assumes when the user is eg. standing or sitting up-right.

At a distance from the inlet opening, ie. in the lower portion of the bag member, the bag is designed with a discharge portion 6 having a discharge opening, not shown in detail, through which the bag may be emptied of its contents by means of a closure device 7 which in the embodiment shown is designed as a valve but which as well be designed in any other way.

In order to bring the bag from the discharge position shown in FIG. 1, in which the bag may be emptied of its contents by opening the closure device, to a position of use, in which the bag is closed and at least a part of the discharge portion including the closure device is brought into a position, in which it does not protrude from the outer contours of the bag member, the collecting bag comprises an accommodating means generally designated 8. The function and structure of the accommodating means will be described in detail further on.

Figure 3:
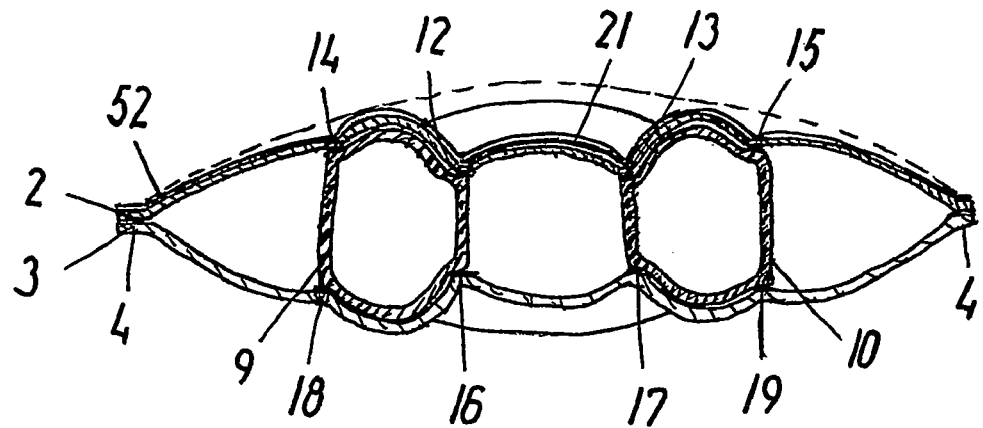
FIG. 3 is a cross-sectional view of the collecting bag along the line III-III in FIG. 2.
Figure 4:
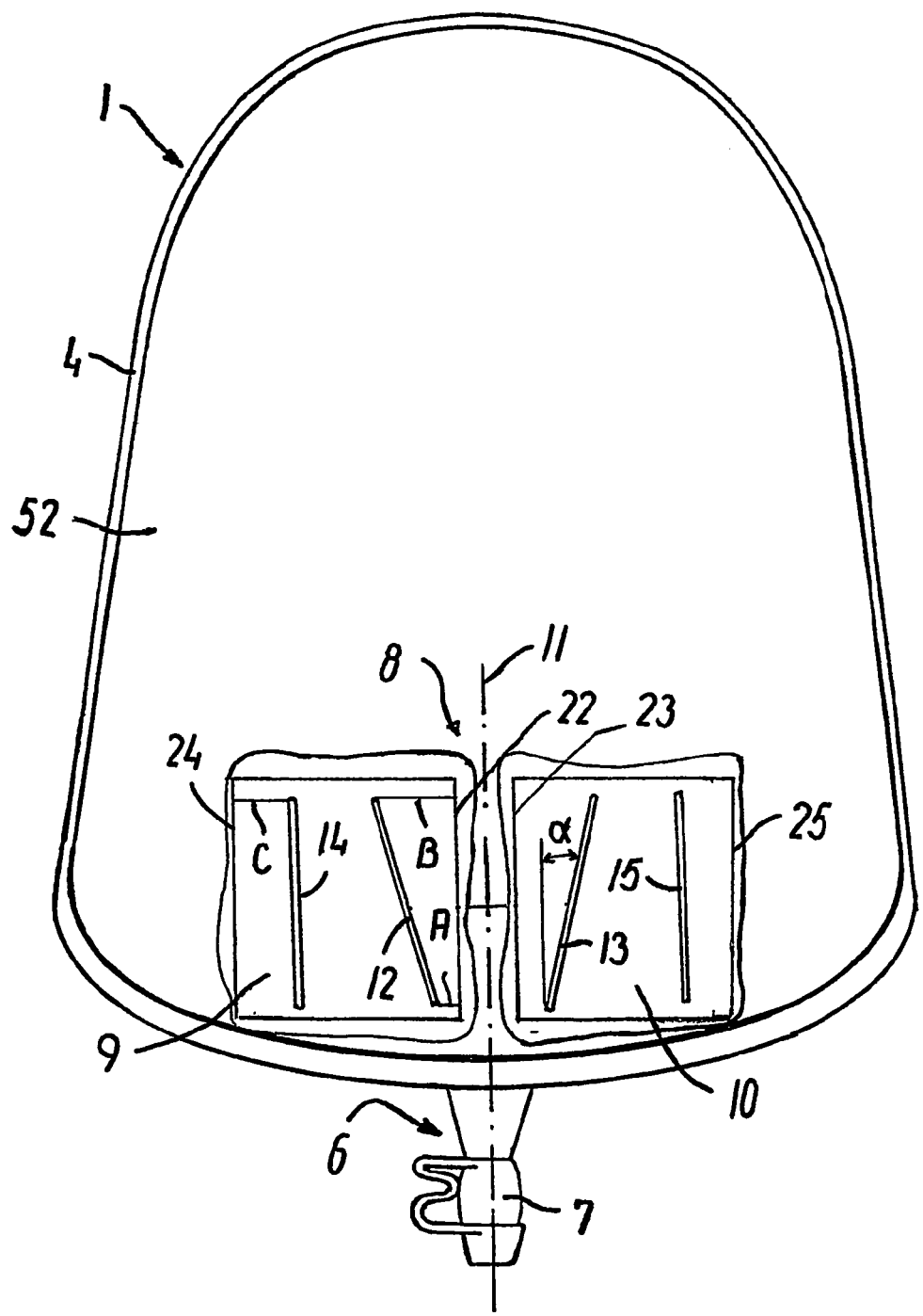
FIG. 4 shows a plan view, partly sectional, of the collecting bag shown in FIG. 1, the bag being shown in the shape it assumes when the bag is empty.

As appears most clearly from FIGS. 3 and 4 the bag member comprises a number of substantially tubular inner film elements 9 and 10. Collecting bags and manufacturing methods for producing bags having such substantially tubular inner film elements are the subject of Applicant's international published application WO 93/17643, and will not be described in detail in the present application. It is noted that the term 'tubular' should be interpreted in its broadest sense, ie. as comprising any element having at least one cavity. Each substantially tubular inner film element may thus be composed of one tube-shaped film blank or several blanks connected with each other.

In the embodiment shown in the drawings, a first and a second substantially tubular inner film element 9 and 10 are provided in the lower part of the bag member 1, ie. near the discharge portion 6, substantially symmetrically with respect to a dividing line 11 substantially parallel with a longitudinal direction defined by the discharge portion 6. In this case the dividing line coincides with the longitudinal direction of the discharge portion and forms a symmetry line of the bag member, and is indicated with a dash-and-dot line.

Each substantially tubular inner film element 9,10 is attached to the inner sides of the front and back film blanks 2 and 3 by means of joints 12-19 provided by means of eg. welding or heat-sealing, eg. in a manner described in the above-mentioned international application. Each substantially tubular inner film element comprises a distal 24, 25 and a proximal 22,23 fold with respect to the dividing line 11 when the bag is substantially empty, ie. in the condition shown in FIG. 4. It is noted that the term 'fold' only refers to the approximate shape the substantially tubular inner film element assumes in the empty condition of the bag. In the embodiment shown in FIGS. 1-6, at least the joints 12-15 between the first and the second tubular film elements 9,10 and the front film blank 2 comprise joint sections 12,13 that extend obliquely, ie. at an angle, with respect to the dividing line. The oblique joint sections situated proximal to the dividing line converge in the direction of the discharge portion, such that the distance A between the end of the lower part of the proximal joint section 12 and the proximal fold 22 is smaller than the distance B between the end of the upper part of the proximal joint section 12 and the proximal fold 22. In this embodiment, the distal joint section 14 extends substantially in parallel with the distal fold 24 such that the distance C is substantially uniform throughout the distal joint section. Preferably, the distance C is smaller than distance B but larger than distance A.

The angle of inclination α between each oblique joint section and the dividing line may be varied but preferably lies in the range from 5° to 60°. In the embodiment shown, the angle is approx. 20°

Preferably, the distance between the lower ends of the oblique joint sections 12,13 substantially corresponds to the cross-sectional dimensions of the corresponding part of the discharge portion.

As indicated in FIG. 3, the substantially tubular inner film elements form open-ended compartments, in which the contents of the bag may be received. Further substantially tubular inner film elements may be formed on each side of the first and second tubular film elements 9,10, near the seam 4, or above or below the first and second tubular film elements in the vicinity of the inlet opening.

Between the oblique sections of the first and second substantially tubular inner film elements the accommodating means 8 for receiving at least a part of the discharge portion including the closure device is formed.

The accommodating means includes a slit 20 formed in the comfort layer 52, through which the closure device 7 of the discharge portion 6 may be inserted.

Due to the inclination of the joint sections 12,13 with respect to the dividing line 11, the bag member will assume such a shape in the at last partly filled condition in the area of the accommodating means that the thickness of the bag element measured between the front and back wall and corresponding to the inner dimensions of the substantially tubular inner film element in question, is smaller at the lower end of these joint sections than at the upper end. The thickness of the compartment formed by the substantially tubular inner film element is defined by measures A, B and C, respectively, the thickness in the lower end at the proximal joint section being 2×A and in the upper end of this section 2×B, whereas the thickness at the distal joint section being 2×C.

The thickness variation between the upper and the lower end is dependent on the angle of inclination of the joint section and entails that the closure device may be lodged in the space provided between the oblique joint sections of the first and second substantially tubular inner film elements. This means that the closure device will not protrude outside the arched plane defined by the overall shape of the bag member, indicated by dashed line in FIG. 3, as the compartments formed by the tubular inner film elements themselves will have a larger extent in the thickness direction.

Figure 5:
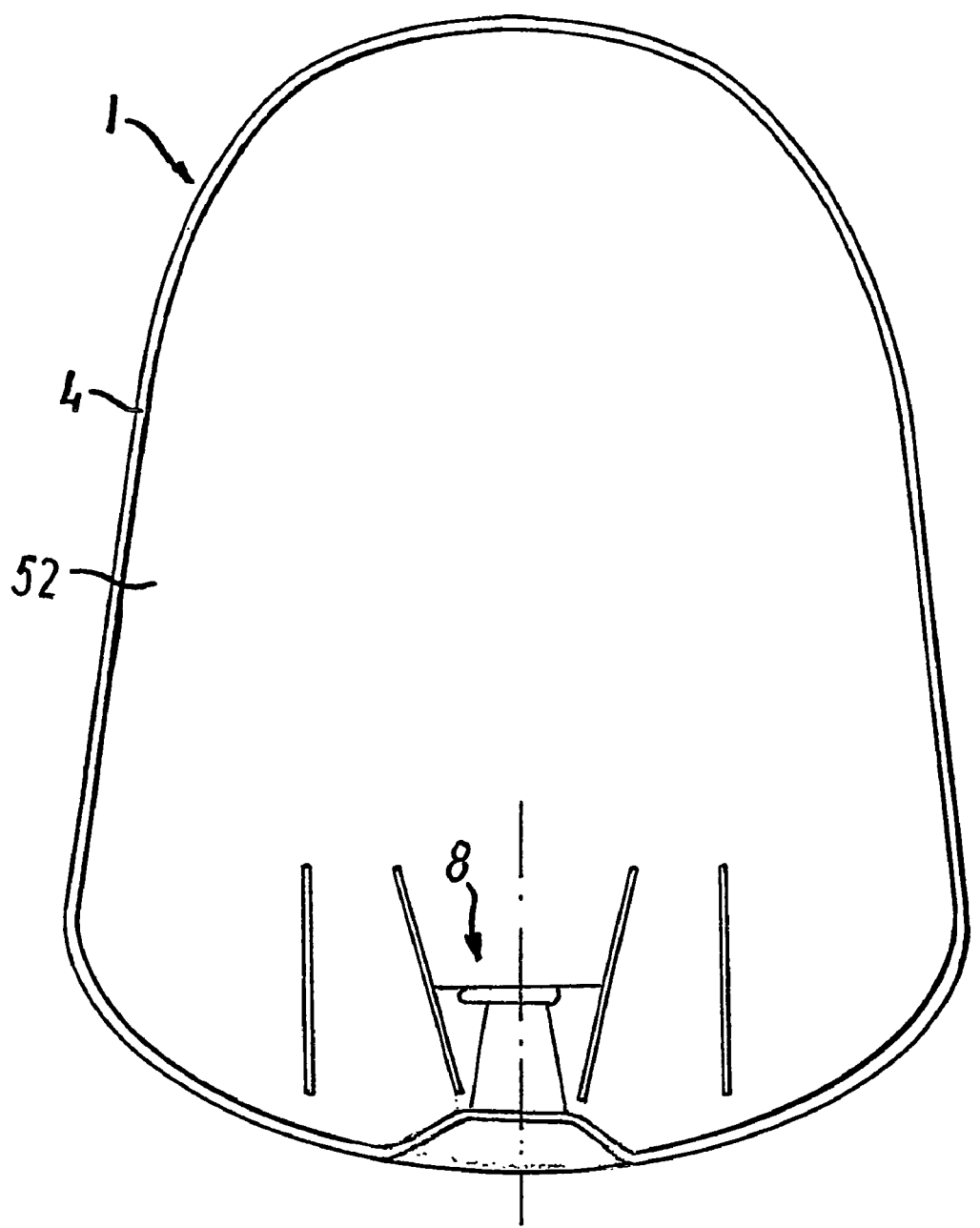
FIG. 5 shows a plan view of the collecting bag shown in FIG. 1 in a position of use.

In order to bring the collecting bag from the position shown in FIGS. 1 to 4, to the position shown in FIG. 5, the discharge portion 6 is folded near its connection with the bag member 1 and the free end of the closure device 7 is inserted into the slit 20. Normally, the closure device 7 is positioned into the accommodating means 8 immediately after emptying of the bag, ie. when the bag member 1 is substantially flat. However, it is also possible to place the closure device 7 in the accommodating means when the bag is filled.

The combination of the substantially wedge-shaped space between the oblique joint sections and the outer film blank, and the pressure exerted on the closure device by the element providing the opening, in which the closure device is inserted, entails that the closure device is pressed into the bag member when the bag is filled.

The second substantially tubular inner film element may be attached to the front film blank in a substantially symmetrical manner.

Figure 6:
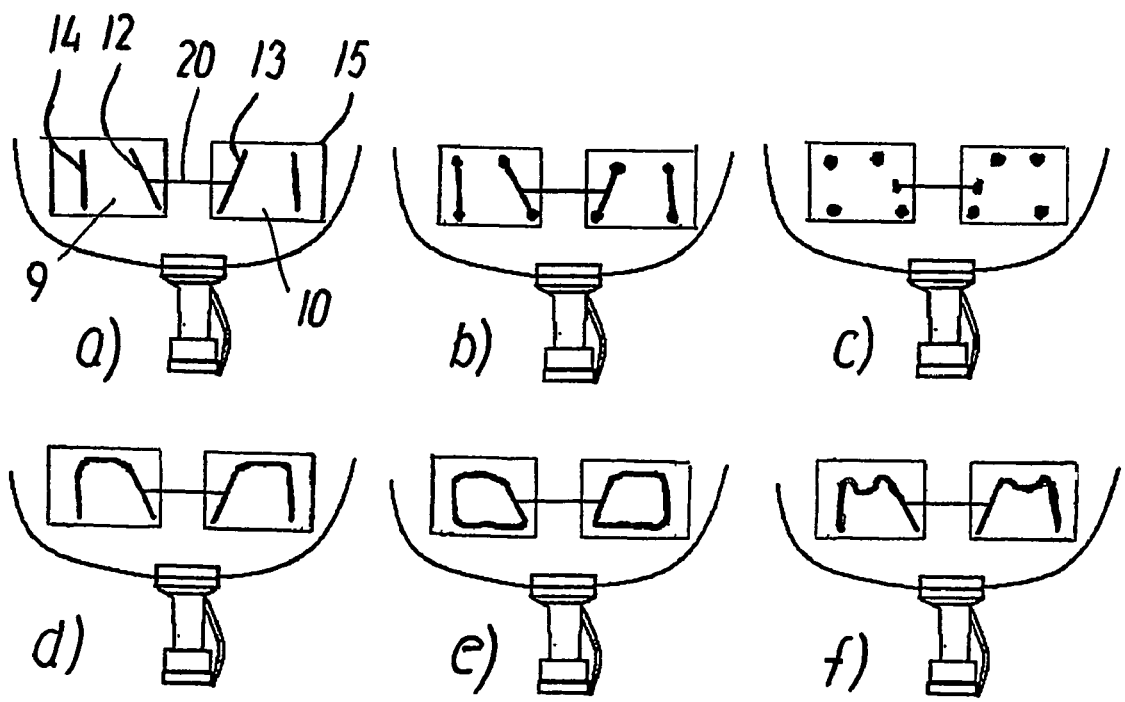
FIGS. 6a-f show, very schematically and at a smaller scale, views corresponding to a part of FIG. 4 of alternative designs of the joints.

Alternative designs of the joints are shown in FIG. 6. FIG. 6a corresponds to the embodiment described in the above, whereas FIG. 6b illustrates how the ends of the joints may be reinforced by means of spots containing reinforcing material or by spot welding. FIG. 6c illustrates how a connection between the substantially tubular inner film elements and the outer film blank may be carried out by means of spot welding, the oblique joint section thus extending between two spots. FIGS. 6d-6f illustrate that the joints may be carried out as continuous welds.

The angle of inclination α of the obliquely extending joint sections is chosen in accordance with the acceptable reduction of the volume available for body wastes, a smaller angle thus reducing the available volume less than a larger angle. Obviously, the angle of inclination is likewise dependent on the dimensions of the tubular film element.

Figure 7:
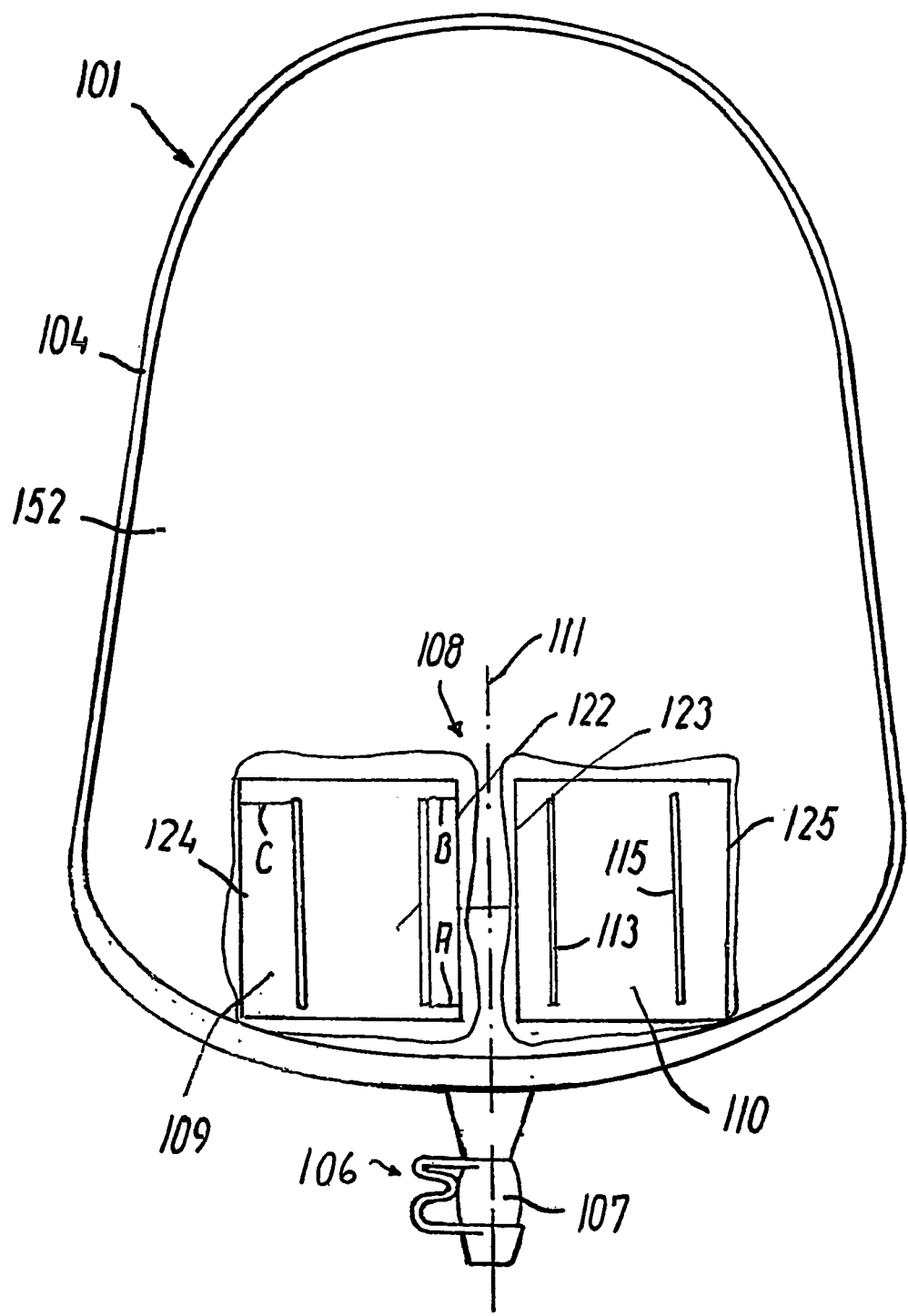
FIG. 7 shows a view corresponding to FIG. 4 of an alternative embodiment of the collecting bag according to the invention.

In FIG. 7, an alternative embodiment of the collecting bag is shown. The element has several structural similarities with the first embodiment shown in FIGS. 1-6. Hence, elements having the same or analogous function as in the first embodiment carry the same reference numerals to which 100 has been added and only differences from the first embodiment will be described in detail.

In this embodiment, the proximal joint section 112 is substantially parallel with the proximal fold 122, such that the distance A,B between the proximal joint section and the proximal fold is substantially uniform. The distance A,B is smaller than the distance ⁻C between the distal joint section 114 and the distal fold 124.

The distance between the proximal joint sections substantially corresponds to the cross-sectional dimensions of the corresponding part of the discharge portion.

By forming the joint sections substantially in parallel with the folds, a substantially uniform height of the bag is achieved in this area.

The connection between the substantially tubular inner film elements and the back film blank may be carried out in a manner corresponding to the joints with the front film blank, or in a different manner, and may be varied as described in the above.

Furthermore, it is of course conceivable, although not preferred, to form the accommodating means on the backside of the bag element, ie. the side which is intended to face the user when the collecting bag is worn.

The element providing the opening for receiving the closure device could in principle consist of a strip-shaped element extending between and being attached to the outer film blank by means of the proximal joint sections. The closure device would thus be inserted under the lower edge of such a strip-shaped element.

In order to secure that the element in question, whether a strip-shaped element or, as described in the embodiment shown in the drawings, the comfort layer 52, is not destroyed during use, eg. by tearing, a reinforcing layer 21 may be inserted between the element and the film blank as shown in FIG. 3. The presence of the proximal joint sections on either side of the accommodating means furthermore entails that a possible widening of the slit in its longitudinal direction is effectively prevented.

The opening for receiving the closure device, ie. the lower edge of the strip-shaped element or the slit 20 in the comfort layer, is formed at such a distance from the discharge portion that the closure device may be comfortably inserted without requiring a large amount of dexterity or entailing risk of damaging any parts of the discharge portion or the comfort layer.

The slit may as shown extend substantially perpendicularly to the dividing line. If it is considered appropriate, the slit may have any suitable inclination with respect to the dividing line as long as the slit extends between the proximal joint sections of the first and second substantially tubular inner film elements such that it is possible to lodge the discharge portion in the space provided between these sections.

The invention should not be regarded as being limited to the embodiment described in the above but various modifications may be carried out without departing from the scope of the following claims.

For example, although the invention has been described only with reference to one kind of closure device, viz. a valve, it is of course possible to apply it to other forms of closure devices comprising eg. clamps or adhesive connections.

The invention claimed is:

1. A collecting bag for human body wastes, comprising:
   a bag member including at least two outer film blanks with joined edges defining the outer contours of the bag member, said outer contours defining a fluid-retaining area of said bag member;
   an inlet opening provided in one of said film blanks;
   a discharge portion at a distance from the inlet opening, in a lower portion of the bag member, including a closure device for bringing the bag from a discharge position, in which the bag is open, to a position of use, in which the bag is closed, the discharge portion defining a longitudinal direction;
   an accommodating element within the outer contours of the bag member for accommodating at least a part of the discharge portion in the position of use of the bag;
   at least a first substantially tubular inner film element and a second substantially tubular inner film element, each substantially tubular inner film element being within said fluid-retaining area of said bag member and attached to the inner side of each outer film blank by means of at least one joint, said first and second substantially tubular inner film elements being respectively situated on each side of a dividing line substantially parallel with the longitudinal direction defined by the discharge portion, each of said substantially tubular inner film elements having, when the bag is substantially empty, a distal fold and a proximal fold with respect to said dividing line;
   a first joint between the first substantially tubular inner film element and one outer film blank and a second joint between the second substantially tubular inner film element and said one outer film blank each respectively including at least one proximal joint section at or near the proximal fold and at least one distal joint section at or near the distal fold, for each of said first and second joints a first distance between at least a lower part of the proximal joint section and the proximal fold being smaller than a second distance between at least a lower part of the distal joint section and the distal fold;
   said accommodating element providing at least one opening for receiving at least a part of the discharge portion in the position of use of the bag, said opening extending substantially transversely between the proximal joint sections of the first and the second substantially tubular inner film elements, respectively; and
   said proximal joint sections defining a recessed space therebetween that overlies the longitudinal dividing line, said recessed space being in the lower portion of the bag adjacent said discharge portion and fully accommodating said closure device in the in-use position so that said closure device when received within said opening does not protrude outside an arched plane defined by an overall shape of said bag member.

2. The collecting bag as claimed in claim 1, wherein at least the proximal joint sections between the first and second substantially tubular inner film elements, respectively, and said one outer film blank extend obliquely with respect to said dividing line such that said proximal joint sections converge in the direction of the discharge portion to define said recessed space.

3. The collecting bag as claimed in claim 2, wherein the second distance between the distal joint section and the distal fold is larger than the first distance between the lower part of the proximal joint section and the proximal fold and smaller than a third distance between the upper part of the proximal joint section and the proximal fold.

4. The collecting bag as claimed in claim 2, wherein an angle of inclination between each oblique joint section and the dividing line lies in the range from 50° to 600°.

5. The collecting bag as claimed in claim 2, wherein a distance between the lower ends of the oblique joint sections substantially corresponds to the cross-sectional dimensions of the corresponding part of the discharge portion.

6. The collecting bag as claimed in claim 1, wherein each proximal joint section is substantially parallel with its respective proximal fold, such that the first distance between the proximal joint section and the proximal fold is substantially uniform along a length of said proximal joint section, and wherein said first distance is smaller than the second distance between the distal joint section and the distal fold.

7. The collecting bag as claimed in claim 6, wherein a distance between the proximal joint sections substantially corresponds to the cross-sectional dimensions of the corresponding part of the discharge portion.

8. The collecting bag as claimed in claim 1, wherein said accommodating element is a comfort layer overlying said one outer film blank, and wherein said at least one opening is provided by a slit in said comfort layer.

9. The collecting bag as claimed in claim 8, wherein a reinforcing layer is inserted between said one outer film blank and said comfort layer, at least in the area of said slit.

10. The collecting bag as claimed in claim 1, wherein each of said joint sections is reinforced by a reinforcing portion.

11. The collecting bag as claimed in claim 1, wherein additional substantially tubular inner film elements are provided in the bag member.

12. The collecting bag as claimed in claim 1, wherein both substantially tubular inner film elements are provided in the area of the bag member situated adjacent the discharge portion.

13. The collecting bag as claimed in claim 1, wherein said bag member is substantially symmetrical with respect to said dividing line.

14. A collecting bag for human body wastes, comprising:
a bag member including at least two outer film blanks with joined edges defining outer contours of the bag member and a fluid-retaining area within said bag member;
an inlet opening provided in one of said film blanks;
a discharge portion at a distance from the inlet opening, in a lower portion of the bag member, including a closure device for bringing the bag from a discharge position, in which the bag is open, to a position of use, in which the bag is closed, the discharge portion defining a longitudinal direction;
an accommodating element within the outer contours of the bag member for accommodating at least a part of the discharge portion in the position of use of the bag;
at least a first and a second substantially tubular inner film element, each substantially tubular inner film element being enclosed within said bag member in said fluid-retaining area and being attached to the inner side of each outer film blank by a respective pair of spaced joint sections, said first and second substantially tubular inner film elements being respectively situated at a respective side of a dividing line that is substantially parallel with the longitudinal direction defined by the discharge portion and each substantially tubular inner film element being provided in the lower portion of the bag member adjacent the discharge portion;
said accommodating element including an element providing at least one opening for receiving at least a part of the discharge portion in the position of use of the bag, said opening extending substantially transversely between said respective pairs of joint sections of the first and the second substantially tubular inner film elements, respectively.

15. The collecting bag as claimed in claim 14, wherein at least the joint sections of each pair of joints that are proximal to said dividing line extend obliquely with respect to said dividing line such that lower ends of said proximal joint sections converge in the direction of the discharge portion, said oblique joint sections shaping the bag when it is at least partly filled so that a bag thickness measured between the two outer film blanks from front to back is smaller at said lower ends where said proximal joint sections converge than at upper ends of said proximal joint sections.

16. The collecting bag as claimed in claim 15 wherein an angle of inclination between each oblique joint section and the dividing line lies in the range from 50° to 60°.

17. The collecting bag as claimed in claim 16, wherein a distance between the proximal joint sections substantially corresponds to cross-sectional dimensions of a corresponding part of the discharge portion.

18. The collecting bag as claimed in claim 14, wherein said accommodating element is a comfort layer overlying at least one outer film blank, said opening being provided by a slit in said comfort layer.

19. The collecting bag as claimed in claim 18, wherein a reinforcing layer is inserted between said one outer film blank and said comfort layer, at least in the area of said slit.

20. The collecting bag as claimed in claim 14, wherein said bag member is substantially symmetrical with respect to said dividing line.

21. The collecting bag as claimed in claim 15, wherein said smaller bag thickness at said proximal joint section lower ends provides a recessed space between the oblique joint sections adjacent the discharge portion in which said closure device is fully accommodated in the in-use position so that said closure device when received in said opening does not protrude outside an arched plane defined by the overall shape of the bag member.

* * * * *